United States Patent
Chung et al.

(10) Patent No.: US 9,662,485 B2
(45) Date of Patent: May 30, 2017

(54) ENSURED COMPONENT BONDING

(71) Applicant: Fenwal, Inc., Lake Zurich, IL (US)

(72) Inventors: Terry Chung, Kildeer, IL (US); Kwang Suk Kim, Palatine, IL (US); James Darren Roxas, Chicago, IL (US); David Shao Ling, Vernon Hills, IL (US)

( * ) Notice: Subject to any disclaimer, the term of this patent is extended or adjusted under 35 U.S.C. 154(b) by 715 days.

(21) Appl. No.: 13/785,985

(22) Filed: Mar. 5, 2013

(65) Prior Publication Data

US 2013/0324974 A1 Dec. 5, 2013

Related U.S. Application Data

(60) Provisional application No. 61/653,352, filed on May 30, 2012, provisional application No. 61/656,358, filed on Jun. 6, 2012.

(51) Int. Cl.
| | |
|---|---|
| *A61M 25/00* | (2006.01) |
| *A61M 25/16* | (2006.01) |
| *A61M 25/18* | (2006.01) |
| *A61M 39/00* | (2006.01) |
| *A61M 39/10* | (2006.01) |
| *A61M 39/12* | (2006.01) |

(52) U.S. Cl.
CPC ........ *A61M 39/1011* (2013.01); *A61M 39/12* (2013.01)

(58) Field of Classification Search
CPC .. A61M 39/1011; A61M 39/12; A61M 39/10; A61M 2039/1027; A61M 25/0014; A61M 2039/0009; A61M 39/00; A61M 2039/1077
See application file for complete search history.

(56) References Cited

U.S. PATENT DOCUMENTS

| | | | | |
|---|---|---|---|---|
| 4,163,722 | A * | 8/1979 | Cosentino et al. | 210/236 |
| 4,417,753 | A * | 11/1983 | Bacehowski | A61J 1/10 156/272.2 |
| 4,473,369 | A * | 9/1984 | Lueders | A61M 39/1011 285/419 |
| 5,330,449 | A * | 7/1994 | Prichard et al. | 604/533 |
| 7,347,913 | B2 | 3/2008 | Dallapiazza | |
| 2004/0254513 | A1* | 12/2004 | Shang et al. | 604/5.01 |
| 2007/0282166 | A1* | 12/2007 | Ayala | A61B 1/00137 600/123 |
| 2010/0087705 | A1* | 4/2010 | Byers et al. | 600/104 |

OTHER PUBLICATIONS

Fenwal, Genesis Tube Sealers product information sheet, 2011, 2 pages.

* cited by examiner

*Primary Examiner* — Edelmira Bosques

(57) ABSTRACT

A tube connector includes a flexible member that engages an inserted length of tubing. The flexible member is configured to adhere to the tubing in the presence of an applied solvent, thereby forming a hermetic seal.

20 Claims, 2 Drawing Sheets

ENSURED COMPONENT BONDING

CONTINUITY DATA

The present application claims the benefit of U.S. Provisional Patent Application No. 61/653,352, entitled "ENSURED COMPONENT BONDING," and filed May 30, 2012, the entirety of which is hereby incorporated by reference. The present application also claims the benefit of U.S. Provisional Patent Application No. 61/656,358, entitled "ENSURED COMPONENT BONDING," and filed Jun. 6, 2012, the entirety of which is hereby incorporated by reference.

BACKGROUND

In some applications, fluid flowing through conduits in a system may be divided into separate streams by a connector that has a single input and multiple outputs. For example, a y-connector (e.g., a connector having a single input and two outputs) may divide fluid flowing through a single conduit into two streams. Such connectors may also be used to combine fluid streams. For example, a y-connector may also be used to combine two streams of fluids into a single stream.

In medical settings, a biological fluid or medicament may be withdrawn from a subject or provided to a subject via a fluid system. For example, apheresis machines are generally configured to separate blood extracted from a subject into its constituent components (e.g., red blood cells, platelets, plasma, etc.). The blood or blood components may then be routed via a fluid system into different collection bags. Such conduits are often permanently bonded to connectors with a solvent adhesive. An incomplete bond or connection between the conduits and connectors may result in leaks and the contamination of the fluids in the fluid system. For example, collected blood or blood components may leak from the conduit if an improper connection is made between a conduit and a connector. Such an incomplete connection may be a result of a variety of factors, including insufficient surface area between the conduit and the connector, insufficient interference between the conduit and the connector, or an incorrect amount of solvent.

SUMMARY

One embodiment relates to a tube connector for a fluid handling system. The connector includes a rigid housing forming an opening configured to receive a length of tubing and forming a hollow channel extending from the opening into the housing. The connector also includes a flexible member configured to receive the length of tubing and extending from the housing into the hollow channel. The flexible member has an engagement portion substantially conforming to the shape of the hollow channel and a tapered portion having a diameter less than an outer diameter of the tubing. The flexible member is formed using a material configured to adhere to the tubing in the presence of a solvent.

Another embodiment relates to a tube connector assembly for a fluid handling system. The assembly includes a length of tubing and a rigid connector housing forming an opening configured to receive the length of tubing and forming a hollow channel extending from the opening into the housing. The assembly also includes a flexible member configured to receive the length of tubing and extending from the housing into the hollow channel. The flexible member has an engagement portion substantially conforming to the shape of the hollow channel and a tapered portion having a diameter less than an outer diameter of the tubing prior to insertion of the tubing into the connector housing. The assembly further includes a solvent configured to form an adhesive bond between the flexible member and the length of tubing.

A further embodiment relates to a tube connector for a fluid handling system. The connector includes means for receiving an inserted length of tubing. The connector also includes means for retaining the inserted length of tubing and forming a hermetic seal with the tubing in the presence of a solvent.

BRIEF DESCRIPTION OF THE DRAWINGS

Features, aspects, and advantages of the present invention will become apparent from the following description, appended claims, and the accompanying exemplary embodiments shown in the drawings, which are briefly described below.

Like reference numbers and designations in the various drawings indicate like elements.

DETAILED DESCRIPTION

It is to be understood that the following detailed description is exemplary and explanatory only, and is not restrictive of the invention as claimed. One or more embodiments may allow for an improved bonding between components of a fluid handling system. While primarily described herein with reference to a fluid handling system used in an apheresis machine, the described concepts may be applied to any other type of fluid handling system that use tubing and connectors. Other exemplary fluid handling systems may include, but are not limited to, fluid handling systems used in dialysis machines, systems configured to remove a biological fluid from a subject (e.g., blood, urine, etc.), systems configured to supply a biological fluid to a subject, systems configured to provide a medicament to a subject, and other such systems.

Figure 1:
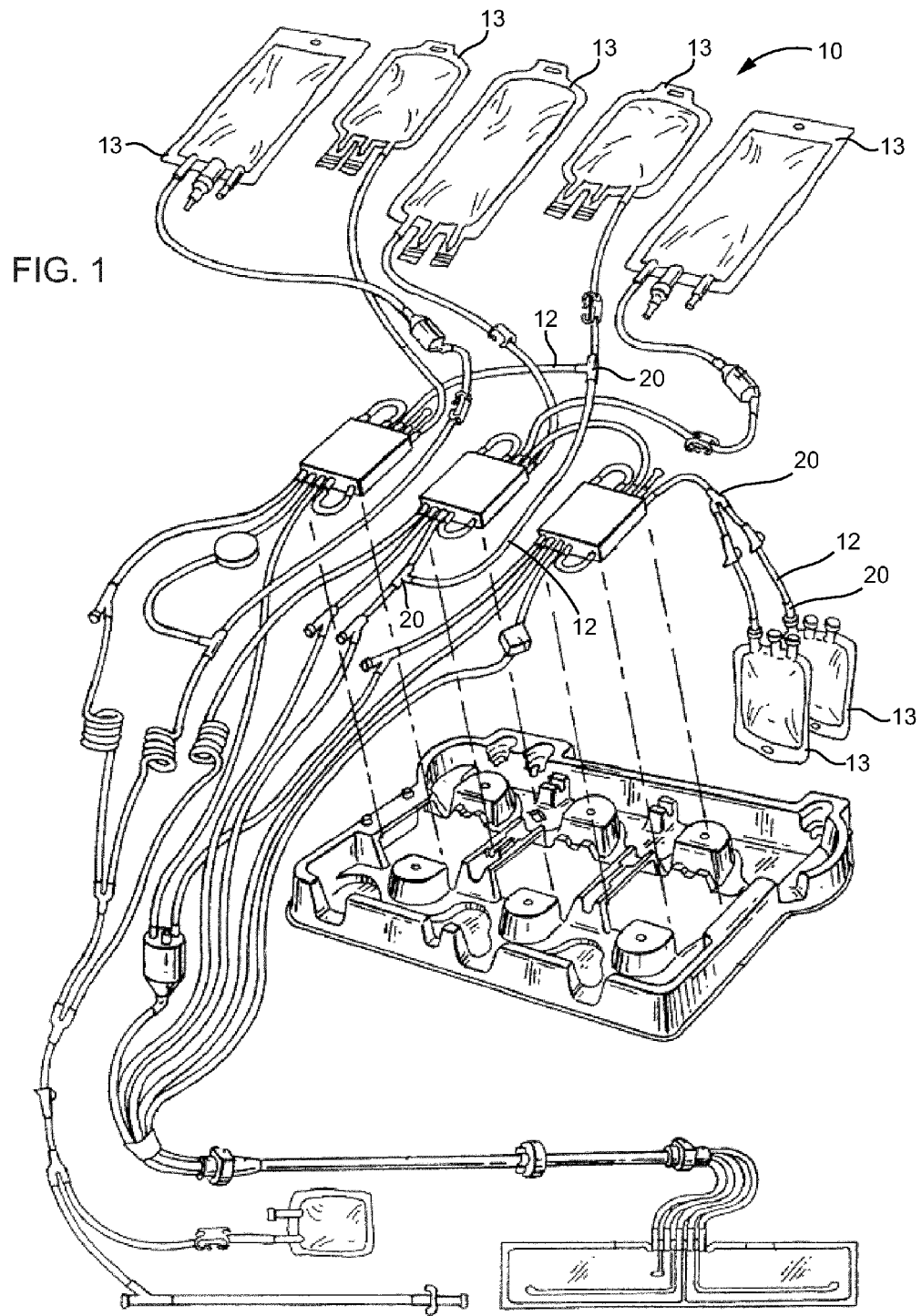
FIG. 1 is an exploded view of a fluid handling system, in accordance with an exemplary embodiment.

Referring now to FIG. 1, a fluid handling system 10 is shown, according to an exemplary embodiment. In various embodiments, fluid handling system 10 is part of an apheresis machine that separates blood drawn from a subject into blood components. For example, an apheresis machine may include a centrifuge or other blood separation device that processes whole blood or other suspensions of biological material into its constituent components (e.g., red blood cells, plasma, platelets, etc.). The apheresis machine may also include fluid handling system 10 which is configured to convey fluid between the subject of the procedure, the centrifuge or other separation device, and/or multiple collection bags 13. Such fluids are routed in fluid handling system 10 via lengths of tubing 12. According to various embodiments, tubing 12 is formed of non-reactive materials that are suitable for handling biological fluids such as blood and may be configured for a single use (e.g., intended to be disposed after each use). Tubing 12 may also be formed of a relatively flexible material, such as PVC or silicone, in some embodiments. In one exemplary embodiment, tubing 12 is a PVC tubing with an outer diameter of less than 3 cm.

Tubing 12 may be coupled to the various components of fluid handling system 10 or to other lengths of tubing 12 via connectors 20. In various embodiments, connectors 20 may be in-line connectors coupling two lengths of tubing 12 together, Y-connectors or T-connectors coupling more than two lengths of tubing 12 together, connectors configured to couple a length of tubing 12 to the apheresis machine, connectors configured to couple a length of tubing 12 to a collection bag 13, or a connector for coupling a length of tubing 12 to any number of lengths of tubing 12. As shown, a connector 20 and a length of tubing 12 are permanently bonded together to form a hermetic seal, thereby preventing or minimizing the escape of fluid from fluid handling system 10 where the length of tubing 12 and the connector 20 are joined. After the collection of the fluids is complete, collection bags 13 may be separated from fluid handling system 10 using a tube sealer that separates and seals lengths of tubing 12 connected to collection bags 13. In other words, fluid handling system 10 may be intended for, and used as, a single-use collection system.

Figure 2:
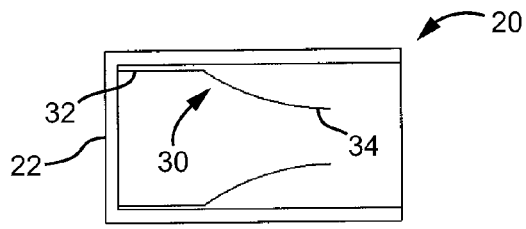
FIG. 2 is a schematic cross section view of a connector for a fluid system, in accordance with an exemplary embodiment.

Referring now to FIG. 2, a schematic cross section view of a connector 20 is shown, according to an exemplary embodiment. Connector 20 may be used in a fluid handling system, such as fluid handling system 10 shown in FIG. 1 or in another such fluid handling system. Connector 20 is generally configured to receive and retain an inserted length of tubing, thereby forming a hermetic seal and preventing fluid from leaving the fluid handling system.

In some embodiments, connector 20 is a generally hollow, cylindrical body with an opening 22 configured to receive a length of tubing. In other embodiments, opening 22 may have any other generally hollow shape (e.g., square, ovoid, etc.), depending on the shape of the tubing to be inserted. Connector 20 may also include a flexible member 30 having an engagement portion 32 that generally conforms to the interior shape of connector 20 and a tapered portion 34 that extends away from the interior wall of opening 22. For example, portion 32 may be cylindrical in shape, if the interior 24 of connector 20 is also cylindrical in shape. As shown, engagement portion 32 is coupled to connector 20 proximate to the opening 22. In one embodiment, flexible member 30 is coupled to connector 20 with a solvent adhesive. In other embodiments, flexible member 30 may be coupled to connector 20 by another suitable method, such as a welded connection or a mechanical connection (e.g., clamped or compressed between two portions of connector 20), or connector 20 may be overmolded around flexible member 30. Engagement portion 32 may have a diameter that is larger than, or approximately equal to, the diameter of the tubing to be inserted into connector 20. Tapered portion 34 extends inward from engagement portion 32 and has a gradually decreasing diameter that is less than the diameter of the tubing to be inserted. In one embodiment, tapered portion 34 may have a parabolic profile. In another embodiment, tapered portion 34 may have a different shape (e.g., a frustoconical shape, etc.).

Figure 3A:
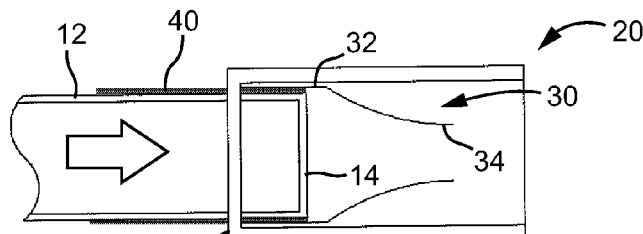
FIG. 3A is a schematic cross section view of a length of tubing partially inserted into the connector of FIG. 2, in accordance with an exemplary embodiment.

Referring now to FIG. 3A, a schematic cross section view of a length of tubing 12 partially inserted into connector 20 is shown, in accordance with an exemplary embodiment As shown, an end 14 of tubing 12 may be inserted into opening 22 of connector 20 and received by engagement portion 32. Tubing 12 may be formed of a relatively flexible material, such as a PVC material with a hardness of approximately 70 shore A. In one embodiment, connector 20 may be constructed using a relatively stiff material, such as polycarbonate, in comparison to that of tubing 12.

According to various embodiments, tubing 12 is bonded to connector 20 using an adhesive compound. The quality of the adhesive bond between tubing 12 and connector 20 is influenced by the relative uncompressed diameters of the tubing 12 and opening 22 (e.g., an interference fit between tubing 12 and connector 20), the insertion depth of tubing 12 in connector 20 (e.g., the bonding surface area), and the amount of a proper solvent in the bonding area between tubing 12 and connector 20.

Flexible member 30 may be a bladder or sleeve inside a rigid body of connector 20. In one embodiment, flexible member 30 may be smooth and may have a high friction property. Flexible member 30 may comprise polyurethane or PVC, suitable for solvent bonding (e.g., with cyclohexanone or another solvent). In some embodiments, flexible member 30 may be constructed using urethane, which is tackier than PVC and would restrict entry of tubing 12 in the absence of solvent 40. A film of flexible member 30 may be smooth to further increase friction.

A layer of solvent 40 may be applied to the outer surface of the tubing 12 and/or to the flexible member 30 to adhere tubing 12 to connector 20. In various embodiments, solvent 40 acts as a lubricant to ease the insertion of tubing 12 into connector 20 and facilitates the creation of a chemical bond between tubing 12 and flexible member 30. The type of solvent used may be varied, depend on the materials of tubing 12 and flexible material 30 and may be one solvent, a blend of solvents, or a blend of solvents and solids. In other embodiments, non-PVC solvents may be used for solvent 40. For example, cyclohexanone may be used as a solvent for bonding polyurethane or PVC tubing (e.g., tubing 12) to a polyurethane or PVC bladder/sleeve (e.g., flexible member 30). In another example, cumene may be used as a solvent for polyolefin (compounded with SEBS (styrene-ethylene-butylene-styrene)) tubing to a polyolefin (compounded with SEBS) bladder/sleeve.

Flexible member 30 (e.g., retainer, bladder, insert, sleeve, etc.) may be provided on the interior of connector 20 and located between the inner diameter of connector 20 and the outer diameter of tubing 12, to increase the quality of the adhesive bond between tubing 12 and connector 20. In some cases, flexible member 30 may also indicate when an incomplete adhesive bond has been formed. In some embodiments, flexible member 30 is a membrane or thin-walled body formed using a material such as plasticized PVC, urethane or polyurethane. Flexible member 30 may act as a gate that allows the end 14 of tubing 12 to be inserted into connector 20 but impedes the removal of tubing 12 from connector 20. In other words, flexible member 30 may further increase the interference with tubing 12. The material used to construct flexible member 30 may have a flexibility of 70 shore A, while other more rigid portions of connector 20 are constructed using materials having flexibilities in the shore D range or are multiple times more rigid. Flexible member 30 may also be constructed using a material which is less flexible than tubing 12.

Figure 3B:
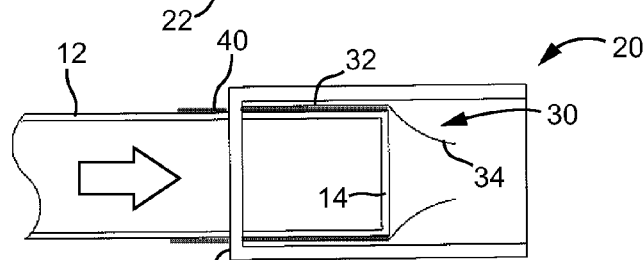
FIG. 3B is a schematic cross section view of the length of tubing of FIG. 3A making contact with the tapered portion of the connector of FIG. 2, in accordance with an exemplary embodiment.

Referring now to FIG. 3B, a schematic cross section view of tubing 12 making contact with the tapered portion 34 of flexible member 30 is shown, in accordance with an exemplary embodiment. As tubing 12 is inserted further into connector 20, end 14 of tubing 12 is received by tapered portion 34 of flexible member 30. In some embodiments, tapered portion 34 has a diameter decreasing from a maximum diameter (e.g., a diameter up to substantially the diameter of opening 22) to a minimum diameter that is less than the outer diameter of end 14 of tubing 12. An interference is therefore created between tubing 12 and flexible member 30. Solvent 40 may act as a lubricant that allows end 14 to be inserted through the tapered portion 34, stretching flexible member 30 around tubing 12. According to various embodiments, tapered portion 34 may also indicate whether an insufficient amount of solvent 40 has been applied. For example, if an insufficient amount of solvent 40 has been applied to tubing 12 to lubricate the entry of end 14 into flexible member 30, the interference between tapered portion 34 and tubing 12 will be too great and tubing 12 will not be able to be inserted into the connector 20.

Figure 3C:
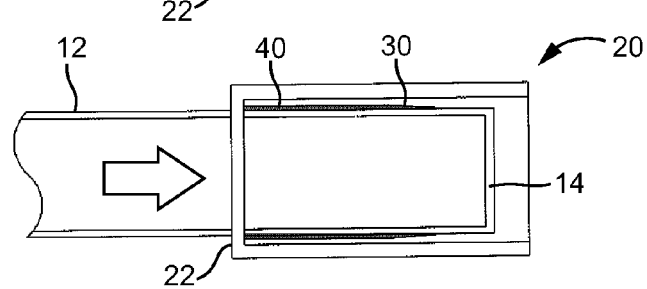
FIG. 3C is a schematic cross section view of the length of tubing of FIGS. 3A-3B fully inserted into the connector of FIG. 2, in accordance with an exemplary embodiment.

Referring now to FIG. 3C, a schematic cross section view of tubing 12 fully inserted into connector 20 is shown, in accordance with an exemplary embodiment. When tubing 12 is fully inserted into connector 20, flexible member 30 is stretched around end 14 of tubing 12, with the solvent 40 compressed between flexible member 30 and tubing 12. Through the interconnection of tubing 12, flexible member 30, and connector 20, a hermetic seal between tubing 12 and connector 20 may be formed. In other words, solvent 40 may cause flexible member 30 to adhere to tubing 12 such that fluid flowing through tubing 12 and connector 20 does not escape.

Figure 4A:
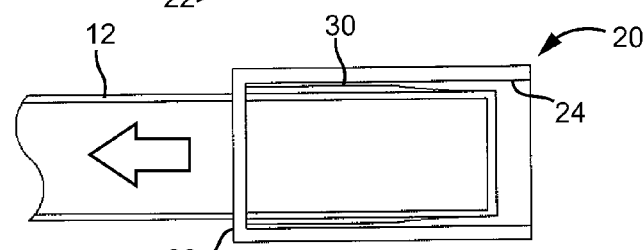
FIG. 4A is a schematic cross section view of the length of tubing of FIGS. 3A-3C bonded to the connector of FIG. 2, in accordance with an exemplary embodiment.
Figure 4B:
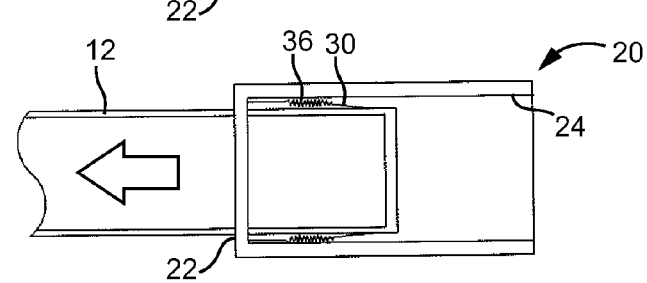
FIG. 4B is a schematic cross section view of the bonded tubing of FIG. 4A being retained by the connector of FIG. 2, in accordance with an exemplary embodiment.

Referring now to FIGS. 4A-4B, schematic cross section views of tubing 12 bonded to connector 20 are shown, according to exemplary embodiments. Once tubing 12 is bonded to the flexible member 30 by solvent 40, flexible member 30 prevents tubing 12 from being withdrawn through opening 22 of connector 20. One end of the flexible member 30 (e.g., the tapered portion 34) is coupled to the tubing 12 while the opposite end (e.g., engagement portion 32) is coupled to the connector 20, thereby preventing tubing 12 from being easily withdrawn from connector 20. As shown in more detail in FIG. 4B, if tubing 12 is moved back out of the connector 20, flexible member 30 will begin to fold back and bunch up on itself, creating an obstruction 36 that prevents further movement of the tubing 12 relative to the connector 20.

While incomplete contact may be formed between tubing 12 and a relatively rigid body, such as the connector 20, the contact area between flexible member 30 and tubing 12 is maximized. The flexible member 30 is distorted (e.g., stretched) to allow tubing 12 to be inserted into connector 20. Further, flexible member 30 may prevent the full insertion of tubing 12 into the connector 20 without the presence of a solvent 40, in some embodiments. Tapered portion 34 of flexible member 30 may provide a tactical indication that tubing 12 is fully inserted into connector 20, thereby reducing the likelihood that tubing 12 will be inadvertently inserted only partially into connector 20 and be only minimally coupled to connector 20.

The construction and arrangement of the elements of the connector as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. Some like components have been described in the present disclosure using the same reference numerals in different figures. This should not be construed as an implication that these components are identical in all embodiments; various modifications may be made in various different embodiments. It should be noted that the elements and/or assemblies of the enclosure may be constructed from any of a wide variety of materials that provide sufficient strength or durability, in any of a wide variety of colors, textures, and combinations.

Additionally, in the subject description, the word "exemplary" is used to mean serving as an example, instance or illustration. Any embodiment or design described herein as "exemplary" is not necessarily to be construed as preferred or advantageous over other embodiments or designs. Rather, use of the word exemplary is intended to present concepts in a concrete manner. Accordingly, all such modifications are intended to be included within the scope of the present inventions. Other substitutions, modifications, changes, and omissions may be made in the design, operating conditions, and arrangement of the preferred and other exemplary embodiments without departing from the spirit of the appended claims.

While the exemplary embodiments are shown with respect to a blood flow distribution device, the connector may in alternative embodiments be implemented in a system for diverting other fluids, such as consumable fluids (e.g., beverages, syrups, etc.) or may be used in a manufacturing setting to approximately evenly distribute a single flow of a fluid to a plurality of destinations for the fluid. Any number of finished goods containers can be coupled to the connector to receive the fluids.

What is claimed is:

1. A tube connector assembly for a fluid handling system comprising:
   a length of tubing;
   a rigid connector housing forming an opening configured to receive the length of tubing and forming a hollow channel extending from the opening into the housing;
   a flexible member configured to receive the length of tubing and extending from the housing into the hollow channel, the flexible member comprising an engagement portion conforming to a shape of the hollow channel and a tapered portion having a diameter less than an outer diameter of the tubing prior to insertion of the tubing into the connector housing; and
   a solvent forming an adhesive bond between the flexible member and the length of tubing, wherein the flexible member has a portion bunched up on itself between the length of tubing and rigid connector housing as a result of a force applied to the tubing along an axis of the tubing, wherein the bunched up portion increases a retention force holding the tubing within the housing.

2. The tube connector assembly of claim 1, wherein the engagement portion of the flexible member has a diameter that is between the diameter of the opening and the outer diameter of the tubing.

3. The tube connector assembly of claim 1, wherein the tapered portion of the flexible member has a parabolic profile.

4. The tube connector assembly of claim 1, wherein the flexible member is formed using the same material as the tubing.

5. The tube connector assembly of claim 4, wherein the flexible member and the tubing are formed using at least one of: plasticized polyvinyl chloride (PVC), urethane or polyurethane.

6. The tube connector assembly of claim 5, wherein the solvent comprises cyclohexanone.

7. The tube connector assembly of claim 4, wherein the flexible member and the tubing are formed using polyolefin.

8. The tube connector assembly of claim 7, wherein the solvent comprises cumene.

9. The tube connector assembly of claim 1, wherein the flexible member comprises a sleeve.

10. The tube connector assembly of claim 1, wherein the flexible member comprises a sleeve and wherein the tapered portion of the sleeve, in response to receiving the length of tubing, is stretchable from a curved tapering shape to a cylindrical shape.

11. The tube connector assembly of claim 1, wherein, the flexible member comprises a sleeve and wherein the tapered portion of the sleeve, in response to receiving the length of the tubing, is stretchable from a first curved tapering shape to a second shape in which the tapered portion extends parallel to an inner wall of the rigid housing.

12. The tube connector assembly of claim 1, wherein the engagement portion of the flexible member comprises a sleeve having an outer circumferential surface extending parallel to an inner wall of the rigid connector housing.

13. The tube connector assembly of claim 1, wherein the tapered portion has varying interior diameter and terminates at an axial end having an axial edge, the varying interior diameter being smallest at the axial edge at the axial end such that an inner surface of the tapered portion at the axial end adjacent the axial edge contacts the length of tubing.

14. The tube connector assembly of claim 1, wherein the flexible member comprises:
 a first opening at a first end of the flexible member adjacent the engagement portion, the first opening facing in a first direction;
 a second opening at a second end of the flexible member opposite the first end, the second opening being adjacent the tapered portion and being smaller than the first opening, wherein the tapered portion tapers in a first direction towards the second opening and wherein the length of tubing extends in the first direction from a location exterior to the rigid connector housing, through the first opening and through the second opening to a terminal end of the length of tubing that is beyond the second end of the flexible member while within the rigid connector housing.

15. The tube connector assembly of claim 14, wherein the first end and the second end of the flexible member are within an interior of the rigid connector housing.

16. The tube connector assembly of claim 14, wherein the length of tubing has an axial end opening facing in the first direction.

17. The tube connector assembly of claim 1, wherein the flexible member has a first end and a second end opposite the first end, wherein the first end and the second end of the flexible member are within an interior of the rigid connector housing.

18. The tube connector assembly of claim 1, wherein the bunched up portion comprises a portion of the tapered portion.

19. The tube connector assembly of claim 1, wherein the engagement portion of the flexible member extends from an end of the rigid connector housing and wherein the bunched up portion comprises a portion of the engagement portion.

20. The tube connector assembly of claim 1, wherein the length of tubing comprises a portion received within the rigid connector housing having a uniform inner diameter along its entire length.

* * * * *